US006074647A

United States Patent [19]
Zimmerman et al.

[11] Patent Number: 6,074,647
[45] Date of Patent: *Jun. 13, 2000

[54] METHOD OF INCREASING SKIN CELL RENEWAL RATE USING ACEROLA CHERRY FERMENTATE

[75] Inventors: Amy C. Zimmerman, Grand Rapids; Daniel V. Beio, Ada, both of Mich.

[73] Assignee: Amway Corporation, Ada, Mich.

[ * ] Notice: This patent is subject to a terminal disclaimer.

[21] Appl. No.: 09/060,435

[22] Filed: Apr. 14, 1998

[51] Int. Cl.$^7$ ..................................................... A61K 7/00
[52] U.S. Cl. ........................ 424/195.1; 424/70.1; 424/74; 424/401
[58] Field of Search ............................... 424/195.1, 70.1, 424/74, 135.1, 401

[56] References Cited

U.S. PATENT DOCUMENTS

| | | | |
|---|---|---|---|
| Re. 33,993 | 7/1992 | Grollier et al. | 424/74 |
| 3,012,942 | 12/1961 | Morse | 167/81 |
| 3,012,943 | 12/1961 | Morse | 195/2 |
| 3,086,915 | 4/1963 | Morse | 195/2 |
| 4,014,995 | 3/1977 | Juliano et al. | 424/168 |
| 4,238,509 | 12/1980 | Evans et al. | 424/358 |
| 4,278,656 | 7/1981 | Nagai et al. | 424/62 |
| 4,363,815 | 12/1982 | Yu et al. | 424/274 |
| 4,369,174 | 1/1983 | Nagai et al. | 424/62 |
| 4,548,728 | 10/1985 | Franklin | 252/174.14 |
| 4,722,843 | 2/1988 | Vinson | 424/195.1 |
| 4,806,365 | 2/1989 | Nakashima | 426/17 |
| 4,851,252 | 7/1989 | Greither et al. | 426/599 |
| 4,877,627 | 10/1989 | Leitz et al. | 426/285 |
| 4,883,659 | 11/1989 | Goodman et al. | 424/78 |
| 4,919,921 | 4/1990 | Hatae | 424/62 |
| 5,171,571 | 12/1992 | Stephan et al. | 424/195.1 |
| 5,262,153 | 11/1993 | Mishima et al. | 424/62 |
| 5,262,762 | 11/1993 | Bormann et al. | 424/195.1 |
| 5,281,196 | 1/1994 | Sultenfuss | 604/20 |
| 5,296,500 | 3/1994 | Hillebrand | 514/562 |
| 5,352,389 | 10/1994 | Gazzani | 252/544 |
| 5,362,494 | 11/1994 | Zysman et al. | 424/401 |
| 5,427,775 | 6/1995 | Sakai et al. | 424/401 |
| 5,441,740 | 8/1995 | Ozlen | 424/401 |
| 5,449,519 | 9/1995 | Wolf et al. | 424/401 |
| 5,747,006 | 5/1998 | Zimmerman et al. | 424/62 |
| 5,888,521 | 3/1999 | Zimmerman | 424/401 |

FOREIGN PATENT DOCUMENTS

| | | |
|---|---|---|
| 2 597 337 | 10/1987 | France . |
| 2 720 643 | 12/1995 | France . |
| 195 15 609 C1 | 4/1996 | Germany . |
| 62-208236 | 9/1987 | Japan . |
| 62-208267 | 9/1987 | Japan . |
| 2-200610 | 8/1990 | Japan . |
| 5-207865 | 8/1993 | Japan . |
| 7-61915 | 3/1995 | Japan . |

OTHER PUBLICATIONS

Ozier C.W. In: Cosmetics Science and Technology. Edited by Edward Sagarin. Interscience Publishers, Inc. 1957. pp. 213–214.

Search results from Teltech® Literature Search Service re Skin Whiteners, Apr. 4, 1996, pp. 1–49.

Report of a Case of Acute Infant Scurvy Treated with Acerola Jelly, C.F. Asenjo Ph. D. and O. Gonzalez–Alvarez, M.D., 1955.

Ascorbic Acid Content and Other Characteristics of the West Indian Cherry, Conrado F. Asenjo and Carlos G. Moscoso, Department of Chemistry and Nutrition School of Tropical Medicine and Department of Plant Breeding, Agricultural Experiment Station, University of Puerto Rico, Food Research, vol. 15, Jan.–Dec., 1950, pp. 103–106.

Acerola Juice Ready for Commercial Production, Journal of Agricultural and Food Chemistry, Nov. 10, 1954, vol. 2, No. 23, p. 1155.

Skin Lightening, A review of melanin formation and the isolation of a new ingredient for products that minimize skin discolorations due to excessive melanin production, Ok–Sub Lee, Eun–Joung Kim, Cosmetics & Toiletries® magazine, vol. 110, Oct. 1995, pp. 51–56.

Chemical Abstract, No. 122(21)264022r, Kinetics Of Anthocyanin Decomposition In Acerola Juice, Author(s): Harvey T. Chan, Jr., and Harry Y. Yamamoto, Journal: ASEAN Food J., 1994, vol. 9, No. 4, pp. 132–135.

Chemical Abstract, No. 121(17)198461j, Effects Of Growth Regulators Applied At Blooming Time On Fruit Quality Of Acerola, *Malpighia emerginata* dc., Author(s) Kiyotake Ishihata and Saburo Ito, Journal: Nettai Nogyo, 1994, vol. 38, No. 2, pp. 113–118.

Chemical Abstract, No. 120(23) 297204(p), Nutrient–Supplying Foods Containing Vitamin C, Inventor (Author): Togo Kuroiwa; Patent: Japan Kokai Tokkyo Koho; JP 9422727 A2; dated Feb. 1, 1994.

Chemical Abstract, No. 120(17) 215777r, Acerola Juice as Acidulant in Preparation of Frozen Desserts, Inventor (Authors): Hiroshi Yamane; Teruaki Myazaki and Kyoshi Takada; Japan Kokai Tokyo Koho JP 93344846 A2; dated Dec. 27, 1993.

Chemical Abstract, No. 120(16) 200486w, Dialysis System for Large Intestine, Method of Use, and Filtrate Solution Composition, Inventor (Author): Andrew Stone, Patent: PCT International WO 9403215; dated Feb. 17, 1994.

(List continued on next page.)

*Primary Examiner*—Sandra E. Saucier
*Assistant Examiner*—Vera Afremova
*Attorney, Agent, or Firm*—Brinks Hofer Gilson & Lione

[57] ABSTRACT

The present invention relates to a composition for topical use comprising a organic acid and acerola cherry fermentate. The present invention also relates to a method of enhancing the rate of skin desquamation by incorporating acerola cherry fermentate into a composition containing an organic acid. The composition can be topically applied.

13 Claims, No Drawings

OTHER PUBLICATIONS

Chemical Abstract, No. 120(11)132676f, Volatile Constituents of Acerola, C. Schippa, G. George, R. Fellous, Journal: Parfums, Cosmet., Aromes; 1993, vol. 113, pp. 81–84.

Chemical Abstract, No. 119(23)248618x, Vitamin C–High Nutrition Supplements Preparation from Acerola Fruits, Inventor (Author) Togo Kuroiwa, Patent: Japan Kokai Tokyo Koho JP 93207865 A2, dated Aug. 20, 1993.

Chemical Abstract, No. 118(23)2733z, Carotenoid–Containing Emulsions for Use in Foods Without the Use of Synthetic Agents, Inventor (Author) Lance Elliott Schlipalius, Patent: PCT International WO 9304598 A1; dated Mar. 18, 1993.

Chemical Abstract, No. 118(21) 211546a, Calculation of Juice Content in a Diluted Fruit Juice Beverage, Chester W. Lindsay, Journal: J. AOAC Int., 1993, vol. 76, No. 2, pp. 424–430.

Chemical Abstract, No. 118(1)5952b, Analysis of Acerola, Authors: Shintetu Kuniyoshi, Minoru Suzuki and Hiromichi Hayano, Journal: Kanzei Chuo Bunsekishoho; 1992, vol. 31, pp. 81–85.

Chemical Abstract, No. 117(17)169813n, The Ascorbic Acid Contents of Fruits of Taiwan, Authors: Huei Ing Liu, and Iuan Huei Hwang, Journal: Zhonghua Nongye Yanjiu; 1991, vol. 40, No. 3, pp. 280–290.

Chemical Abstract, No. 115(25)278390b, Change in Vitamin C During the Fermentation of Acerola Vinegar, Makoto Nakamura, Journal: Nippon Shokuhin Kogyo Gakkaishi, 1991, vol. 38, No. 8, pp. 691–694.

Chemical Abstract, No. 114(19)184032p, Ascorbic Acid Content in Acerola Fruit From Different Production Regions in Relation to Degree of Maturity and Its Stability During Processing, Author(s): Saburo Itoo, Mitsuko Aiba, Kiyotake Ishihata; Journal: Nippon Shokuhin Kogyo Gakkaishi; 1990, vol. 37, No. 9, p. 726–9.

Chemical Abstract, No. 114(18)170990n, Water Purifying Agent, Inventor (Author) Norio Someya, Patent: Japan Kokai Tokyo Koho JP 90268885A2; dated Nov. 2, 1990.

Chemical Abstract, No. 110(23)211306(g), Vinegar Enriched With Vitamin C and Its Manufacture, Inventor (Author) Todomu Nakashima, Patent: United States Pat. No. 4,806,365 dated Feb. 21, 1989.

Chemical Abstract, No. 108(26)226675j, Cosmetic Containing Antioxidants to Delay the Aging of Skin, Inventor (Author) Olivier Courtin, Patent: French Patent No. FR 2597337 dated Oct. 23, 1987.

Chemical Abstract, No. 104(25)223741j, Pesticide Tolerances for Glyphosate, Corporate Author: United States Environmental Protection Agency, Journal: Federal Regist., 1986, vol. 51, No. 78, pp. 15325–15326.

Chemical Abstract, No. 100(9)66734g, Pesticide Programs, Tolerances for Pesticide Chemicals in or on Raw Agricultural Commodities, Paraquat, Corporate Author: United States Environmental Protection Agency, Journal: Fed. Regist., 1984, vol. 49, No. 4, p. 882.

Chemical Abstract, No. 72(13)65961v, Root Development of Acerola Trees as Affected by Liming, Authors: Ernesto Hernandez–Medina, J. Velez–Santiago, M.A. Lugo–Lopez, Journal: J. Agr. Univ. P.R., 1970, vol. 54, No.1, pp. 57–61.

Chemical Abstract, No. 68(1)2091h, Observations on Physical and Chemical Properties of Acerola Fruit and Puree, Author: Brian Ian Brown, Journal: Queensl. J. Agric. Anim. Sci., 1967, vol. 23, No. 4, pp. 599–604.

Chemical Abstract, No. 67(25)115916d, Titrimetric determination of L–Ascorbic Acid in Colored Solutions. I.V. Acerola Cherries and Their Concomitant Use in Fruit Juices, Authors: Rudolf Fischer, G. Freise; Journal: Dtsch. Apoth.–Ztg.; 1967, vol. 107, No. 34, pp. 1175–1176.

Chemical Abstract, No. 66(21)92405z, Factors Affecting Ascorbic Acid Content of the Acerola (*Malphigia Glabra*), Authors: H.Y. Nakasone, R.K. Miyashita, George M. Yamane, Journal: Proc. Am. Soc. Hortic. Sci., 1966, vol. 89, pp. 161–166.

Chemical Abstract, No. 66(5)18134u, Ascorbic Acid Content of Acerola Fruits and Acerola Powder, Ascorbic Acid Determination in the Presence of Reductones, Author: Annelies Schillinger, Journal: Z. Lebensm.–Unters. Forsch, 1966, vol. 131, No. 2.

Chemical Abstract No. 531391, Embase No. 76115593, Therapeutic Use of 'AVENA' Skin Cleansing Preparations, Kuerner H. Karlstr. 29, Karlsruhe Germany West; Z. Hautkr. (Germany, West), 1975, 50/15 (631–635).

Chemical Abstract, No. 12064007, Pascal No. 95–0263947; Oats: Chemistry, Technology and Potential Uses in the Cosmetic Industry; Paton, D.; Bresciani, S.; Nam Fong Han; Hart, J.; Journal: Cosmetics and Toiletries; 1995, 110(3) 63–70 (5 p.).

Chemical Abstract, No. 00911864, Pascal No. 76–0006664; Therapeutischer erfahrungsbericht mit der avena–reihe (Resultats therapeutiques obtenus avec les produits avena); Kurner H. Ankermann & Co. G.M.B.H., Friesoythe, Journal: Z. Hautkrankh, 1975, 50 (15) 631–635.

Chemical Abstract, No. 001371746; WPI Acc No: 75–21383W/13; Patent Assignee: Quaker Oats Co.; Priority Data (CC No. Date): US 398651 (730919); US 565695 (750407).

Chemical Abstract, No. 010545082; WPI Acc No. 96–042035/05; Patent Assignee: Clarins; Priority Data (CC No. Date); FR 946837 (940603).

Chemical Abstract, No. 010338357; WPI Acc. No. 95–240445/31; Patent Assignee: Nurture Inc; Priority Data (CC No Date); US 172485 (931223).

Chemical Abstract, No. 010002632; WPI Acc. No. 94–270343/33; Patent Assignee: (Kono) Konovalov II; Priority Data (CC No Date); SU 5016466 (911228).

Chemical Abstract, No. 009708838; WPI Acc. No. 93–402391/50; Patent Assignee: (Aero=) Aerozol sci prodn assoc; (stal=) stalgen agric firm; Priority Data (CC No Data); SU 4868052 (900921).

Chemical Abstract, No. 00362016; Derwent Accession No.: 73–35329; A New Natural Ingredient for Cosmetic Formulators; Assignee: Quaker–Oats (Cleveland Ohio USA); Journal: Drug Cosmet. Ind., 113, No. 3, 48, 50, 52, 54, 56, 1973.

Chemical Abstract, No. 124298400; CA: 124 (22)298400u; Formulating personal care products with hydrolyzed oat protein; Author(s): Loncar, Clifford; Journal: Household Pers. Prod. Ind.; Date: 1996, vol.: 33; No.: 3; pp. 85–87.

Chemical Abstract, No. 124269972; CA: 124(20)269972(b); Hair and Scalp Conditioners Containing Oat Extract and Hydroxy Acids; Inventor (Author) Onitsuka, Satoshi; Dubowoj, Polina; Assignee: Kao Corporation GMBH; Patent: Germany; DE 19515609 C1; Date: Mar. 28, 1996.

Chemical Abstract, No. 123152610; CA: 123(12)152610v; Oat Oil Compositions with Useful Dermatological Properties ; Inventor (Author); Potter, Richard; Castro, James M.; Moffatt, Lori C.; Assignee: Nurture, Inc., Patent: PCT International; WO 9517162 A1; Date: Jun. 29, 1995; pp. 36 pp.

Chemical Abstract, No. 94109095; CA: 94(14)109095b; The Water Oat Extracts as Skin Cosmetics; Assignee: Onodera, Hiroshi; Patent: Japan Kokai Tokkyo Koho JP 80164613; Date: Dec. 22, 1980.

Chemical Abstract, No. 88197417; CA: 88(26)197417n; Cosmetic Ingredients; Author(s): Miller, Aaron; Location: Kalar Lab., Chicago, Ill.; Journal: Soaps, Deterg. Toiletries Rev., Date: 1977; vol.: 7; No.: 9; pp. 21–25.

Chemical Abstract, No. 80030602; CA: 80(6)30602s; New Natural Ingredient for Cosmetic Formulators; Author(s): Coe, John; Juliano, Angelo; Journal: Drug Cosmet. Ind.; Date: 1973; vol.: 113; No.: 3; pp. 48, 50, 52, 54, 56.

Chemical Abstract, No. 0458058; This Cosmetic Company Really Knows Its Oats, Business Week, Feb. 22, 1993; p. 91; No. 3306.

Chemical Abstract, No. 008399002; WPI Acc No: 90–286003/38; Cosmetic Acerola extract—obtd. by washing with water, removing ppte. decolouring and filtering; Patent Assignee: (Nich–) Nichirei KK; Priority Data (CC No. Date): JP 8916185 (Jan. 27, 1989).

Chemical Abstract, No. 007353231; WPI Acc No: 87–350237/50; Two–part skin anti–ageing cosmetic compsn.—contg. active principle hindering skin ageing due to formation and action of free radicals; Patent Assignee: (Cour) Courtin O; (Clar–) Clarins; Priority Data: (CC No Date): FR 8788 (870000); FR 8416038 (Oct. 19, 1984).

Chemical Abstract, No. 108226675; CA: 108(26)226675j; Cosmetic containing antioxidants to delay the aging of skin; Application: FR 8788 (Jan. 7, 1987).

Oats; Chemistry, Technology and Potential Uses in the Cosmetic Industry, High purity oat derivatives show potential as plant–based conditioning ingredients for skin–and hair–care; David Paton and Sandra Bresciani; Agriculture and Agri–Food Canada, Saskatoon, SK, Canada; Nam Fong Han, Canamino, Inc., Ottawa, ON, Canada; Janice Hart, Canamino Inc., Long Island, NY, USA; Cosmetics & Toiletries Magazine, vol. 110, Mar. 1995, pp. 63–70.

METHOD OF INCREASING SKIN CELL RENEWAL RATE USING ACEROLA CHERRY FERMENTATE

BACKGROUND OF THE INVENTION

The present invention relates to a composition to enhance the rate of skin cell renewal or exfoliation and to a method of increasing the skin cell renewal rate. In particular, the present invention relates to a composition containing one or more selected organic acids and an enhancing effective amount of acerola cherry fermentate. The present invention also relates to a method of increasing the rate of skin-cell renewal by applying a composition to the skin, wherein the composition comprises at least one selected organic acid, an enhancing effective amount of acerola cherry fermentate, and optionally, a suitable cosmetic vehicle.

With the aging population there is a continuing effort to provide cosmetic compositions to improve the appearance of the skin. Recently, many compositions have included hydroxycarboxylic acids such as glycolic, lactic, citric, and malic acids and are being marketed for such uses as dry skin, the reduction of wrinkles and fine lines and to combat the effects of aging. In addition, there is always a need for a composition to treat dry skin.

Human skin may be classified into two major parts: the outer layer or epidermis and an underlying layer or dermis. The dermis contains, among other things, blood vessels, nerves, collagen, elastin, and fibroblast cells, which are responsible for the biosynthesis of collagen and elastin.

The epidermis itself also may be considered to consist of two major zones, an inner or malpighian layer and an outer or horny layer. The malpighian layer, a living tissue, may be further divided into basal, spinous, and granular layers. The horny layer, a dead tissue, is also referred to as stratum corneum, which is the skin tissue one feels.

In the natural process, basal cells in the basal layer move outward through the spinous and granular layers to become dead cells called corneocytes, in the stratum corneum. The stratum corneum consists of approximately 14 layers of corneocytes. In the normal skin it takes about 14 days for the basal cells to move from the basal layer to the end of the granular layer and to become corneocytes, and another 14 days to reach the outermost layer of the stratum corneum, where they are naturally shed or exfoliated. This process of forming corneocytes is called keratinization, and stratum corneum are the natural products produced by this process. Usually, it takes about 28 days for cells of the basal layer to move outward to the surface in the course of making new skin.

It is thought that by increasing the natural exfoliation rate of the outermost part of the stratum corneum and thus exposing lower layers of the stratum corneum, the appearance of the skin will be improved. Many substances are known to increase the rate of natural exfoliation but recently hydroxycarboxylic acids have received an increasing amount of attention. A drawback to the use of hydroxycarboxylic acids is that they can irritate the skin of the user. Thus, it would also be desirable to increase the rate of exfoliation beyond that provided by the hydroxycarboxylic acid without further increasing the possibility of skin irritation.

SUMMARY OF THE INVENTION

In accordance with the present invention, there is provided a composition for topical use comprising at least one organic acid and acerola cherry fermentate. The acerola cherry fermentate is present in an amount effective to enhance the skin cell exfoliation rate of the organic acid. It is believed that the acerola cherry fermentate synergistically enhances the rate of skin exfoliation when combined with a organic acid, wherein the organic acid is preferably chosen from hydroxy carboxylic acids, keto carboxylic acids and mixtures thereof.

In accordance with this aspect of the present invention, there is provided a composition comprising at least one organic acid and acerola cherry fermentate present in a therapeutically effective amount in topically acceptable vehicle for application to human skin to enhance the rate of skin exfoliation provided by the organic acid.

Preferably, the composition can be used for the topical treatment and/or alleviation of dry skin and other skin maladies.

Although it is known that the acerola cherry fermentate contains a minor amount of organic acids and a minor amount of carboxylic acids, typically they are present in an amount no greater than about 5% by weight, preferably no greater than about 3%, and more preferably, no greater than about 2% of the acerola cherry fermentate. The acids include lactic, citric, malic, tartaric, ascorbic acids with lactic comprising about 92% by weight of all the acids. Surprisingly, it has been found that when the acerola cherry fermentate is combined with an organic acid, the exfoliation rate is increased beyond that which would be expected from the additional minor amount of acids found in the acerola cherry fermentate.

Surprisingly, the enhancement in the rate of skin exfoliation provided by the acerola cherry fermentate does not cause additional skin irritation.

The terms "minor amount of organic acids" and "minor amount of carboxylic acids" as used in the specification and accompanying claims means that any organic acid or carboxylic acid, which includes saturated and unsaturated carboxylic and dicarboxylic acids, hydroxymonocarboxylicic acids, hydroxydicarboxylic acids, and hydroxytricarboxylic acids, is present in an amount no greater than about 5% by weight, preferably no greater than about 3%, and more preferably, no greater than about 2% of the acerola cherry fermentate.

In the composition according to the present invention, the amount of acerola cherry fermentate to be used can not be absolutely specified because it varies according to the form of preparation. However, it is generally used in an amount from about 0.01% to about 50%, more generally from about 0.1% to about 10%. Preferably the acerola cherry fermentate is used in an amount from about 0.5% to about 8%, more preferably from about 1% to about 5% based on the whole weight of the composition.

It is noted that, unless otherwise stated, all percentages given in this specification and the appended claims refer to percentages by weight.

DETAILED DESCRIPTION OF THE INVENTION

In accordance with the present invention, a skin, hair, and nail composition is provided and comprises at least one organic acid and acerola cherry fermentate. In another aspect, the composition comprises one or more exfoliating agents, and acerola cherry fermentate to enhance the exfoliation effect of the exfoliating agents.

The organic acid is chosen from hydroxy carboxylic acids, keto carboxylic acids and mixtures thereof. The hydroxycarboxylic acids can be any of the known hydroxycarboxylic acids but are preferably 2-hydroxycarboxylic acids and related compounds. For convenience, the 2-hydroxycarboxylic acids and related compounds which may be used in accordance with this invention may be classified into three groups, namely (1) 2-hydroxycarboxylic acids, (2) 2-ketocarboxylic acids and esters thereof, and (3) other related compounds. The related compounds may include hydroxycarboxylic acids with the hydroxyl group at any position other than position 2, for example position 3, position 4 or position 5, as well as cyclic hydroxycarboxylic acids (e.g., ascorbic acid and quinic acid), and also may include ketocarboxylic acids and esters thereof. Preferred related compounds include 3-hydroxycarboxylic acids, and 2-ketocarboxylic acids and esters thereof.

Group 1

The first group comprises organic carboxylic acids in which one hydroxy group is attached to the 2 position carbon atom of the acid. The generic structure of such 2-hydroxycarboxylic acids may be represented as follows:

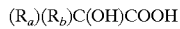

where $R_a$ and $R_b$ may be the same or different and are independently selected from H, F, Cl, Br, alkyl, aralkyl or aryl group of saturated or unsaturated, isomeric or non-isomeric, straight or branched chain or cyclic form, having 1 to 29 carbon atoms, and in addition $R_a$ and $R_b$ may carry OH, CHO, COOH and alkoxy group having 1 to 9 carbon atoms. 2-Hydroxycarboxylic acids may be present as a free acid or lactone form, or in a salt form with an organic base or an inorganic alkali. 2-Hydroxycarboxylic acids may exist as stereoisomers as D, L, and DL forms when $R_a$ and $R_b$ are not identical.

Typical alkyl, aralkyl and aryl groups for $R_a$ and $R_b$ include methyl, ethyl, propyl, isopropyl, butyl, pentyl, octyl, decyl, dodecyl, hexadecyl, benzyl, and phenyl, etc. 2-Hydroxycarboxylic acids of the first group may be further divided into subgroups comprising (1) alkyl hydroxycarboxylic acids, (2) aralkyl and aryl hydroxycarboxylic acids, (3) polyhydroxy-carboxylic acids, and (4) hydroxy-polycarboxylic acids. The following are representative 2-hydroxycarboxylic acids in each subgroup.

(1) Alkyl Hydroxycarboxylic Acids 1. 2-Hydroxyethanoic acid (Glycolic acid, hydroxyacetic acid)
    (H) (H) C (OH) COOH
2. 2-Hydroxypropanoic acid (Lactic acid)
    ($CH_3$) (H) C (OH) COOH
3. 2-Methyl 2-hydroxypropanoic acid (Methyllactic acid)
    ($CH_3$) ($CH_3$) C (OH) COOH
4. 2-Hydroxybutanoic acid
    ($C_2H_5$) (H) C (OH) COOH
5. 2-Hydroxypentanoic acid
    ($C_3H_7$) (H) C (OH) COOH
6. 2-Hydroxyhexanoic acid
    ($C_4H_9$) (H) C (OH) COOH
7. 2-Hydroxyheptanoic acid
    ($C_5H_{11}$) (H) C (OH) COOH
8. 2-Hydroxyoctanoic acid
    ($C_6H_{13}$) (H) C (OH) COOH
9. 2-Hydroxynonanoic acid
    ($C_7H_{15}$) (H) C (OH) COOH
10. 2-Hydroxydecanoic acid
    ($C_8H_{17}$) (H) C (OH) COOH
11. 2-Hydroxyundecanoic acid
    ($C_9H_{19}$) (H) C (OH) COOH
12. 2-Hydroxydodecanoic acid (Alpha hydroxylauric acid)
    ($C_{10}H_{21}$) (H) C (OH) COOH
13. 2-Hydroxytetradecanoic acid (Alpha hydroxymyristic acid)
    ($C_{12}H_{25}$) (H) C (OH) COOH
14. 2-Hydroxyhexadecanoic acid (Alpha hydroxypalmitic acid)
    ($C_{14}H_{29}$) (H) C (OH) COOH
15. 2-Hydroxyoctadecanoic acid (Alpha hydroxystearic acid)
    ($C_{16}H_{33}$) (H) C (OH) COOH
16. 2-Hydroxyeicosanoic acid (Alpha hydroxyarachidonic acid)
    ($C_{18}H_{37}$) (H) C (OH) COOH
17. 2-Hydroxytetraeicosanoic acid (Cerebronic acid)
    ($C_{22}H_{45}$) (H) C (OH) COOH
18. 2-Hydroxytetraeicosenoic acid (Alpha hydroxynervonic acid)
    ($C_{22}H_{43}$) (H) C (OH) COOH (2) Aralkyl and Aryl 2-Hydroxycarboxylic Acids 1. 2-Phenyl 2-hydroxyethanoic acid (Mandelic acid)
    ($C_6H_5$) (H) C (OH) COOH
2. 2,2-Diphenyl 2-hydroxyethanoic acid (Benzilic acid)
    ($C_6H_5$) ($C_6H_5$) C (OH) COOH
3. 3-Phenyl 2-hydroxypropanoic acid (Phenyllactic acid)
    $C_6H_5CH_2$) (H) C (OH) COOH
4. 2-Phenyl 2-methyl 2-hydroxyethanoic acid (Atrolactic acid)
    ($C_6H_5$) ($CH_3$) C (OH) COOH
5. 2-(4'-Hydroxyphenyl) 2-hydroxyethanoic acid (4-Hydroxymandelic acid)
    (HO—$C_6H_4$) (H) C (OH) COOH
6. 2-(4'-Chlorophenyl) 2-hydroxyethanoic acid (4-Chloromandelic acid)
    (Cl-$C_6H_4$) (H) C (OH) COOH
7. 2-(3'-Hydroxy-4'-methoxyphenyl) 2-hydroxyethanoic acid (3-Hydroxy-4-methoxymandelic acid)
    (HO—, $CH_3O$—$C_6H_3$) (H) C (OH) COOH
8. 2-(4'-Hydroxy-3'-methoxyphenyl) 2-hydroxyethanoic acid (4-Hydroxy-3-methoxymandelic acid)
    (HO—, $CH_3O$—$C_6H_3$) (H) C (OH) COOH
9. 3-(2'-Hydroxyphenyl) 2-hydroxypropanoic acid [3-(2'Hydroxyphenyl) lactic acid]
    (HO—$C_6H_4$—$CH_2$) (H) C (OH) COOH
10. 3-(4'-Hydroxyphenyl) 2-hydroxypropanoic acid [3-(4'-Hydroxyphenyl) lactic acid]
    (HO—$C_6H_4CH_2$) (H) C (OH) COOH
11. 2-(3',4'-Dihydroxyphenyl) 2-hydroxyethanoic acid (3,4-Dihydroxymandelic acid)
    (HO—, HO—$C_6H_3$) (H) C (OH) COOH (3) Polyhydroxy-Carboxylic Acids 1. 2,3-Dihydroxypropanoic acid (Glyceric acid)
    ($HOCH_2$) (H) C (OH) COOH
2. 2,3,4-Trihydroxybutanoic acid (Isomers; erythronic acid, threonic acid)
    ($HOCH_2$ HOCH) (H) C (OH) COOH 3. 2,3,4,5-Tetrahydroxypentanoic acid (Isomers; ribonic acid, arabinoic acid, xylonic acid, lyxonic acid)

(HOCH$_2$ HOCH HOCH) (H) C (OH) COOH 4, 2,3,4,5,6-Pntahydroxyhexanoic acid (Isomers; allonic acid, altronic acid, gluconic acid, mannoic acid, gulonic acid, idonic acid, galactonic acid, talonic acid)

(HOCH$_2$ HOCH HOCH HOCH) (H) C (OH) COOH 5. 2,3,4,5,6,7-Hexahydroxyheptanoic acid (Isomers; glucoheptonic acid, galactoheptonic acid etc.)

(HOCH$_2$ HOCH HOCH HOCH HOCH) (H) C (OH) COOH (4) Hydroxy-Polycarboxylic Acids 1. 2-Hydroxypropane-1,3-dioic acid (Tartronic acid)

(HOOC) (H) C (OH) COOH 2. 2-Hydroxybutane-1,4-dioic acid (Malic acid)

(HOOC CH$_2$) (H) C (OH) COOH 3. 2,3-Dihydroxybutane-1,4-dioic acid (Tartaric acid)

(HOOC HOCH) (H) C (OH) COOH 4. 2-Hydroxy-2-carboxypentane-1,5-dioic acid (Citric acid)

(HOOC CH$_2$)$_2$ C (OH) COOH 2,3,4,5-Tetrahydroxyhexane-1,6-dioic acid (Isomers; saccharic acid, mucic acid etc.)

HOOC (CHOH)$_4$ COOH

The 2-hydroxycarboxylic acids may be present in forms other than the acid, such as, for example, salts or lactones. Typical lactone forms which may be used in accordance with this invention include, for example, gluconolactone, galactonolactone, glucuronolactone, galacturonolactone, gulonolactone, ribonolactone, saccharic acid lactone, pantoyllactone, glucoheptonolactone, mannonolactone, and galactoheptonolactone.

Group 2

The second group, which comprises compounds related to the 2-hydroxycarboxylic acids, includes organic carboxylic acids in which one keto group is attached to position 2 carbon atom of the acid. The generic structure of such 2-ketoacids may be represented as follows:

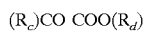

(R$_c$)CO COO(R$_d$)

wherein R$_c$ and R$_d$ can be the same or different and are each selected from H, alkyl, aralkyl or aryl group of saturated or unsaturated, isomeric or non-isomeric, straight or branched chain or cyclic form, having 1 to 29 carbon atoms, and in addition RC may carry F, Cl, Br, I, OH, CHO, COOH and alkoxy group having 1 to 9 carbon atoms. The alpha ketoacids may be present as a free acid or an ester form, or in a salt form with an organic base or an inorganic alkali. The typical alkyl, aralkyl and aryl groups for R$_c$ and R$_d$ include methyl, ethyl, propyl, 2-propyl, butyl, pentyl, hexyl, octyl, dodecyl, hexadecyl, benzyl and phenyl.

In contract to 2-hydroxycarboxylic acids of the first group compounds, the ester form of 2-ketocarboxylic acids has been found to be therapeutically effective for signs and symptoms of cutaneous aging including intrinsic and extrinsic aging. For example, while methyl 2-hydroxypropanoate and ethyl 2-hydroxypropanoate have minimal effects, methyl 2-ketopropanoate and ethyl 2-ketopropanoate are therapeutically very effective. The real mechanism for such difference is not known. We have speculated that the ester form of the 2-ketocarboxylic acid is chemically and/or biochemically very reactive, and a free 2-ketocarboxylic acid may be released in the skin after penetration through the stratum corneum of the skin. The representative 2-ketocarboxylic acids and their esters of the second group are listed below:

1. 2-Ketoethanoic acid (Glyoxylic acid)

(H) CO COOH

2. Methyl 2-ketoethanoate (H) CO COOCH$_3$ 3. 2-Ketopropanoic acid (Pyruvic acid)

CH$_3$ CO COOH

4. Methyl 2-ketopropanoate (Methyl pyruvate)

CH$_3$ CO COOCH$_3$

5. Ethyl 2-ketopropanoate (Ethyl pyruvate)

CH$_3$ CO COOC$_2$H$_5$

6. Propyl 2-ketopropanoate (Propyl pyruvate)

CH$_3$ CO COOC$_3$H$_7$ 7. 2-Phenyl-2-ketoethanoic acid (Benzoylformic acid)

C$_6$H$_5$ CO COOH

8. Methyl 2-phenyl-2 ketoethanoate (Methyl benzoylformate)

C$_6$H$_5$ CO COOCH$_3$

9. Ethyl 2-phenyl-2-ketoethanoate (Ethyl benzoylformate)

C$_6$H$_5$ CO COOC$_2$H$_5$ 10. 3-Phenyl-2-ketopropanoic acid (Phenylpyruvic acid)

C$_6$H$_5$CH$_2$ CO COOH

11. Methyl 3-phenyl-2-ketopropanoate (Methyl phenylpyruvate)

C$_6$H$_5$CH$_2$ CO COOCH$_3$

12. Ethyl 3-phenyl-2-ketopropanoate (Ethyl phenylpyruvate)

C6H$_6$CH$_2$ CO COOC$_2$H$_5$ 13. 2-ketobutanoic acid

C$_2$H$_5$ CO COOH 14. 2-Ketopentanoic acid

C$_3$H$_7$ CO COOH 15. 2-Ketohexanoic acid

C$_4$H$_9$ CO COOH 16. 2-Ketoheptanoic acid

C$_5$H$_{11}$ CO COOH 17. 2-Ketooctanoic acid

C$_6$H$_{13}$ CO COOH 18. 2-Ketododecanoic acid

C$_{10}$H$_{21}$ CO COOH

19. Methyl 2-ketooctanoate

C$_6$H$_{14}$ CO COOCH$_3$

Group 3

The third group, which also comprises related compounds, includes, among others, hydroxycarboxylic acids where the hydroxy is at a position other than position 2, and cyclic hydroxycarboxylic acids which are useful for topical application to improve signs of aging skin and the cutaneous appendages. The members of this group, which are more conveniently identified by name than by generic structures, include salicylic and other beta-hydroxy carboxylic acids as well as, ascorbic acid, quinic acid, isocitric acid, tropic acid (2-phenyl 3-hydroxypropanoic acid), trethocanic acid, 3-chlorolactic acid, citramalic acid, agaricic acid, alcuritic acid, pantoic acid, lactobionic acid and hexulosonic acid.

The acerola cherry is not, in fact, a true cherry but has come to include the cherry-like berries that are produced by any of several shrubs of the Malpighia family. These cherry-like berries are also known by other names depending on where they are produced, for instance, West Indian cherry, Barbados cherry, Surinam cherry, and Cereza. The term "acerola cherry" as used in the specification and appended claims is intended to be generic for all of these different berries of the Malpighia family.

The acerola cherry fermentate used in the present invention contains only a minor amount of organic acids, particularly carboxylic acids, which includes saturated and unsaturated carboxylic and dicarboxylic acids, hydroxymonocarboxylicic acids, hydroxydicarboxylic acids, and hydroxytricarboxylic acids. In particular, any organic acid or carboxylic acid present in the acerola cherry fermentate is present in an amount no greater than about 5% by weight, preferably no greater than about 3%, and more preferably no greater than about 2% of the acerola cherry fermentate.

The acerola cherry fermentate can be made in any suitable manner to achieve an extract that contains only a minor amount of organic acids, preferably less than about 5% of organic acids. The raw acerola cherry used to make the fermentate may be brown, green, yellow, red or a mixture of two or more, depending upon the availability.

Preferably, the acerola cherry fermentate is obtained from Collaborative Laboratories (NY) and it is believed that the process for making the Acerola cherry fermentate useful in the composition of the present invention is as follows. A cherry extract is prepared by washing the bulk cherries, pitting them and then reducing them to a puree, which is subjected to shearing and extraction with water whereby a filtrate is produced. Thereafter, the filtrate is fermented using a bacteria, preferably a bacteria from the lactobacillus family, to produce a fermentate that is separated from the bulk filtrate. The separated fermentate is the acerola cherry fermentate useful in the present invention.

In the composition according to the present invention, the amount of acerola cherry fermentate to be used can not be absolutely specified because it varies according to the form of the preparation. It is, however, generally used in an amount from about 0.01% to about 50%, more generally from about 0.1% to about 10%. Preferably the acerola cherry fermentate is used in an amount from about 0.5% to about 8%, more preferably from about 1% to about 5% based on the whole weight of the composition.

Another aspect of the present invention includes a method of increasing the rate of skin exfoliation or desquamation comprising topically applying a composition containing at least one organic acid and an enhancing effective amount of acerola cherry fermentate. In this aspect, the method includes topically applying to the skin a composition comprising an organic acid and acerola cherry fermentate, in an amount and for a period of time sufficient to increase the rate of natural skin desquamation.

Surprisingly, the advantageous results achieved by the incorporation of the acerola cherry fermentate are realized even though the acerola cherry fermentate contains only a minor amount of organic acids.

To prepare a therapeutic composition in solution form, at least one of the aforementioned organic acids and acerola cherry fermentate are incorporated into pharmaceutically acceptable vehicles. Desirably, the organic acid is selected from the group consisting of lactic acid, malic acid, citric acid, glycolic acid and mixtures thereof.

The concentration of organic acid may range from about 0.01 to about 99 percent by weight of the total composition. Preferably, the concentration of organic acid ranges from about 0.1% to about 70%, more preferably from about 1% to about 15%, and desirably from about 1% to about 10%.

The concentration of the acerola cherry fermentate ranges from about 0.01 to about 99 percent by weight of the total composition. Preferably, the concentration of acerola cherry fermentate ranges from about 0.05% to about 30%, more preferably from about 0.1% to about 10%.

Desirably, the ratio of organic acid to acerola cherry fermentate ranges from about 1:1 to about 100:1. It is believed that when the ratio of the organic acid to the acerola cherry fermentate is within this range that irritation of acid is reduced and cell renewal rate is incremental. Within this ratio, it is desired to have a composition with a pH between about 3.0 and about 5.0, preferably between about 3.5 and about 4.5, more preferably, between about 3.8 and about 4.2.

Therapeutic compositions of the present invention may be formulated as a solution, gel, lotion, cream ointment, or other pharmaceutically acceptable form. The compositions of the present invention may also contain various known and conventional cosmetic ingredients so long as they do not detrimentally affect the desired enhancement of skin desquamation. For example, cosmetic ingredients such as alcohols, fats and oils, surfactants, fatty acids, silicones, humectants, moisturizers, viscosity modifiers, emulsifiers, stabilizers, coloring agents, and perfumes or fragrances may be included.

Examples of suitable fatty acids include those chosen from linoleic acid, γ-linolenic acid, homo-γ-linolenic acid, columbinic acid, eicosa-(n-6,9,13)-trienoic acid, arachidonic acid, α-linolenic acid, timnodonic acid, hexaenoic acid and mixtures thereof.

Non-essential fatty acids can also be employed in addition to or in place of essential fatty acids, examples of which are chosen from myristic, palmitic, stearic and isostearic acids, and mixtures thereof.

The composition according to the invention also comprises a cosmetically acceptable aqueous or non-aqueous vehicle to act as a diluant, dispersant or carrier to facilitate distribution when the composition is applied to the skin, hair and/or nails.

Vehicles other than water can include liquid or solid emollients, solvents, humectants, thickeners and powders. Examples of each of these types of vehicle, which can be used single or as mixtures of one or more vehicles, are as follows:

Emollients, such as stearyl alcohol, glyceryl monoricinoleate, glyceryl monostearate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eiconsanyl alcohol, behenyl alcohol, cetyl palmitate, volatile or non-volatile silicone oils such as dimethylpolysiloxane, di-n-butyl sebacate, isopropyl myristate, isopropyl palmitate, isopropyl stearate, butyl stearate, poethylene glycol, triethylene glycol, lanolin, cocoa butter, corn oil, cotton seed oil, tallow, lard, olive oil, palm kernel oil, rapeseed oil, safflower seed oil, evening primrose oil, soybean oil, sunflower seed oil, passion flower oil, avocado oil, olive oil, sesame seed oil, coconut oil, arachis oil, castor oil, acetylated lanolin alcohols, petroleum jelly, mineral oil, butyl myristate, isostearic acid, palmitatic acid, isopropyl linoleate, lauryl lactate, myristyl lactate, decyl oleate, myristyl myristate;

Propellants, such as air, propane, butane, isobutane, dimethyl ether, carbon dioxide, nitrous oxide;

Solvents such as ethyl alcohol, methylene chloride, isopropanol, acetone, squalane, squalene, ethylene glycol monethyl ether, diethylene glycol monobutyl ether, diethylene glycol monoethyl ether, polyethylene glycol, dimethyl sulphoxide, dimethyl formamide, butylene glycol, tetrahydrofuran;

Powders such as chalk, talc, fullers earth, kaolin, starch, gums, colloidal silica sodium polyacrylate, tetra alkyl and/or trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, ethylene glycol monostearate.

The cosmetically acceptable vehicle will usually form from 10 to 99.9%, preferably from 50 to 99% by weight of the emulsion, and can, in the absence of other cosmetic adjuncts, form the balance of the composition.

Although the composition according to the invention can be aqueous or non-aqueous, a particularly convenient form is an emulsion, in which case an oil or oily material will normally be present, together with an emulsifier to provide a water-in-oil emulsion, an oil-in-water emulsion, or a complex emulsion, depending largely on the average hydrophilic-lipophilic balance (HLB) of the emulsifier employed.

The composition can optionally comprise one or more oils or other materials having the properties of an oil. Examples of suitable oils include mineral oil and vegetable oils, and oil materials, such as those already proposed herein as emollients. Other oils or oily materials include silicone oils, both volatile and non-volatile, such as polydimethyl siloxanes. The oil or oily material, when present for the purposes for forming an emulsion, will normally form up to 90%, preferably from 10 to 80% by volume of the composition.

The composition can also optionally comprise one or more emulsifiers the choice of which will normally determine whether a water-in-oil or and oil-in-water emulsion is formed. When a water-in-oil emulsion is required, the chosen emulsifier or emulsifiers should normally have an average HLB value of from 1 to 6. When an oil-in-water emulsion is required, a chosen emulsifier or emulsifiers should have an average HLB value of >6.

Examples of suitable emulsifiers are set below in Table 1 in which the chemical name of the emulsifiers is given together with an example of a trade name as commercially available, and the average HLB value.

TABLE 1

| Chemical Name of Emulsifier | Trade Name | HLB Value |
|---|---|---|
| Sorbitan trioleate | Arlacel 85 | 1.8 |
| Sorbitan tristearate | Span 65 | 2.1 |
| Glycerol monoleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |
| Poloxyethylene (2) stearyl ether | Brij 72 | 4.9 |
| Poloxyethylene sorbitol beeswax derivative | G-1702 | 5 |
| PEG 200 dilaurate | Emerest 2622 | 6.3 |
| Sorbitan monopalmitate | Arlacel 40 | 6.7 |
| Polyoxyethylene (3.5) nonyl phenol | Emulgen 903 | 7.8 |
| PEG 200 monostearate | Tegester PEG 200 MS | 8.5 |
| Sorbitan monolaurate | Arlacel 200 | 8.6 |
| | 400-DO | 8.8 |

TABLE 1-continued

| Chemical Name of Emulsifier | Trade Name | HLB Value |
|---|---|---|
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monooleate | Neutronyx 834 | 10.4 |
| Polyoxytheylene (20) sorbitan tristearate | Tween 65 | 10.5 |
| Polyoxyethylene (20) sorbitan trioleate | Tween 85 | 11.0 |
| Polyoxytheylene (8) monostearate | Myrj 45 | 11.1 |
| PEG 400 monooleate | Emerest 2646 | 11.7 |
| PEG 400 monostearate | Tegester PEG 400 | 11.9 |
| Polyoxytheylene 10 monooleate | Ethofat 0/20 | 12.2 |
| Polyoxytheylene (10) stearyl ether | Brij 76 | 12.4 |
| Polyoxytheylene (10) cetyl ether | Brij 56 | 12.9 |
| Polyoxytheylene (9.3) octyl phenol | Triton X-100 | 13.0 |
| Polyoxytheylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxytheylene sorbitol lanolin derivative | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxytheylene (20) sorbitan monostearate | Tween | 14.9 |
| Polyoxytheylene 20 sorbitan monooleate | Tween 80 | 15.0 |
| Polyoxytheylene (20) stearyl ether | Brij 78 | 15.3 |
| Polyoxytheylene (20) sorbitan monopalmitate | Tween 40 | 15.6 |
| Polyoxyethylene (20) cetyl ether | Brij 58 | 15.7 |
| Polyoxyethylene (25) oxypropylene monostearate | G-2162 | 16.0 |
| Polyoxytheylene (20) sorbitol monolaurate | Tween 20 | 16.7 |
| Polyoxytheylene (23) lauryl ether | Brij 35 | 16.9 |
| Polyoxytheylene (50) monostearate | Myrj 53 | 17.9 |
| PEG 4000 monostearate | Pegosperse 4000 MS | 18.7 |

The foregoing list of emulsifiers is not intended to be limiting and merely exemplifies selected emulsifiers which are suitable for use in accordance with the invention. It is to be understood that two or more emulsifiers can be employed if desired.

The amount of emulsifier or mixtures thereof, to be incorporated in the composition of the invention, when appropriate is from 1 to 50%, preferably from 2 to 20% and most preferably from 2 to 10% by weight of the composition.

Although the composition of the invention can be anhydrous, it can also comprise water, usually up to 98%, preferably from 5 to 80% by volume.

The composition of the invention can also optionally comprise a high molecular weight silicone surfactant which can also act as an emulsifier, in place of or in addition to the optional emulsifiers already mentioned. One example of a suitable silicone surfactant is a high molecular weight polymer of dimethyl polysiloxane with polyoxyethylene and/or polyoxypropylene side chains having a molecular weight of from 10,000 to 50,000. The dimethyl polysiloxane polymer is may be provided as a dispersion in a volatile siloxane, the dispersion comprising, for example, from 1 to 20% by volume of the polymer and from 80 to 99% by volume of the volatile siloxane. Ideally, the dispersion consists of a 10% by volume of the polymer dispersed in the volatile siloxane. Examples of the volatile siloxanes in which the polysiloxane polymer can be dispersed include polydimethyl siloxane (pentamer and/or hexamer).

A preferred silicone surfactant is cyclomethicone and dimethicone copolyol, such as DC 3225C Formulation Aid available from DOW CORNING. Another is laurylmethicone copolyol, such as DC Q2-5200, also available from Dow Corning.

The amount of silicone surfactant, when present in the composition will normally be from 0.1% to 25%, preferably from 0.5 to 15% by weight of the emulsion.

Examples of other conventional adjuncts which can optionally be employed include preservatives, such as para-hydroxy benzoate esters; antioxidants, such as α-tocopherol, humectants, such as glycerol, sorbitol, 2-pyrrolidone-5carboxylate, dibutylphthalate, gelatin, polyethylene, glycol, preferably PEG 200–600; buffers, such as lactic acid together with-a base such as triethanolamine or sodium hydroxide; surfactants, such as glycerol ethers; waxes, such as beeswax, ozokerite wax, paraffin wax, plant extracts, such as aloe Vera, cornflower, witch hazel, elderflower, cucumber; thickeners; activity enhancers; colorants; perfumes; and sunscreen materials such as ultrafine titanium dioxide and organic sunscreens such as p-aminobenzoic acid and esters thereof, ethylhexyl p-methoxycinnamate, 2-ethoxyethyl p-methoxycinnamate and butyl methoxydibenzoylmethane; and skin benefit agents, such as retinoic acid, retinol, retinol esters; anti-inflammatory agents, such as salicylic acid; skin whiteners, such as arbutin and mixtures thereof.

In accordance with one aspect of the present invention, the rate of natural skin desquamation may be increased by topical application to the skin of the above composition. In this regard, the present invention encompasses a method of enhancing the rate of natural skin desquamation comprising topically applying to the skin a composition comprising a organic acid and acerola cherry fermentate in an amount and for a period of time sufficient to increase the rate of natural skin desquamation. Preferably, the composition is as described above.

Generally, the topical application is on at least a daily basis and may be applied for any suitable period of time. Within a few days, a user may notice improvement in skin texture and smoothness.

The present invention also includes a method of enhancing a composition used for skin desquamation and including a an organic acid wherein the method includes incorporating an enhancing effective amount of acerola cherry fermentate.

The following are illustrative examples of formulations and compositions according to this invention. Although the examples use only selected compounds and formulations, it should be understood that the following examples are illustrative and not limited. Thus, any of the aforementioned organic acids and related compounds may be substituted according to the teachings of this invention in the following examples.

Table 2 sets forth a preferred embodiment of a lotion according to the present invention.

TABLE 2

| INGREDIENT | AMOUNT (wt %) |
|---|---|
| Lactic Acid (88% active) | 4.50 |
| Citric, Malic, and Lactic acid mixture (30–40% active) | 3.00 |
| Acerola Cherry Fermentate (1.8–3% active acid) | 3.00 |
| Glyceryl monostrearate PEG 100 Stearate | 3.00 |
| Sodium Hydroxide | 2.30 |
| Glycerin | 2.00 |
| Butylene Glycol | 2.00 |
| Dimethicone | 2.00 |
| Stearic Acid | 2.00 |
| Phenonip | 0.75 |
| Sorbitan Stearate | 0.50 |
| Magnesium Aluminum Silicate | 0.40 |
| Cetyl Alcohol | 0.25 |
| Xanthan Gum | 0.20 |
| Methylparaben | 0.15 |
| Water and adjuncts | qs to 100.00 |
| TOTAL | 100.00 |

Adjuncts include but are not limited to preservatives such as methyl paraben, phenonip, gums such as magnesium aluminum silicate, hydroxyethyl cellulose, and xanthan gum, humectants such as panthenol, glycerin and butylene glycol, waxes such as sorbitan stearate and glyceryl monostearate and PEG 100 stearate, stearic acid, cetyl alcohol, skin conditioning agents such as alkyl benzoates, dimethicone, lipids, hyaluronic acid and salts thereof, green tea, ginko biloba, polyglyceryl methacrylate, propylene glycol.

Table 3 presents a gel-type formula falling within the scope of the present invention with the amounts provided being expressed as weight percent.

TABLE 3

| INGREDIENT | AMOUNT (wt %) |
|---|---|
| Lactic Acid (88% active acid) | 2.25 |
| Citric, Malic, and Lactic acid mixture (30–40% active) | 3.00 |
| Acerola Cherry Fermentate (1.8–3% active acid) | 3.00 |
| PEG-20 | 5.00 |
| Glycerin | 4.00 |
| Polyglyceryl methacrylate, Propylene Glycol | 4.00 |
| Butylene Glycol | 3.00 |
| Sodium Hydroxide | 1.40 |
| Hydroxyethyl cellulose | 0.40 |
| Xanthan gum | 0.40 |
| Saccharide isomerate | 0.30 |
| Water and adjuncts | qs to 100.00 |
| TOTAL | 100.00 |

In order to determine whether compositions containing organic acids and acerola cherry fermentate were therapeutically effective in enhancing the natural rate of skin desquamation the following tests were conducted. The skin cell renewal, irritation level and therapeutic index were measured according to the procedure described in *Soap/*

*Cosmetics/Chemical Specialties* for September 1993 at pp.55–59.

TABLE 4

| Formula | AHA* % | Acerola Fermentate % | % Cell Renewel | Irritation Level | Therapeutic Index |
|---------|--------|----------------------|----------------|------------------|-------------------|
| A | 3.0 | 0 | 12.2 | 11.4 | 10.7 |
| B | 3.0 | 3.0 | 19.8 | 15.6 | 11.5 |
| C | 3.0 | 3.0 | 21.4 | 16.8 | 12.7 |
| D | 5.0 | 3.0 | 19.8 | 14.2 | 14.0 |
| E | 5.0 | 3.0 | 18.9 | 14.1 | 13.4 |
| F | 5.0 | 3.0 | 22.6 | 13.1 | 17.3 |

*AHA refers to the total amount of active hydroxycarboxylic acid selected from glycolic acid, malic acid, citric acid, lactic acid and mixtures thereof.

Formulas A–E were made according to the formula set forth in Table 2 with the amounts of water and alpha-hydroxy acid being varied so that the alpha-hydroxy acid was present in the amounts shown in Formulas A–E, above. Formula F was made according to the formula set forth in Table 3 with the amount of water and alpha-hydroxy acid varied to the level shown for Formula F. The results show that the addition of the acerola cherry fermentate surprisingly and unexpectedly significantly increased cell renewal rate while only slightly increasing irritation.

It should be understood that a wide range of changes and modifications can be made to the compositions and methods of this invention. It is therefore intended that the foregoing description illustrates rather than limits this invention, and that it is the following claims, including all equivalents, which define this invention.

What is claimed:

1. A method of enhancing the rate of mammalian skin desquamation comprising topically applying to the skin a composition comprising:
   a first organic acid selected from the group consisting of glycolic, malic, citric and salts thereof and mixtures thereof, and
   acerola cherry fermentate, the acerola cherry fermentate containing a minor amount of a second organic acid.

2. The method of claim 1 wherein the acerola cherry fermentate contains less than about 5% of the second organic acid based on the weight of the acerola cherry fermentate.

3. The method of claim 2 wherein the second organic acid is selected from the group consisting of glycolic, malic, citric, and lactic acid, salts thereof and mixtures thereof.

4. The method of claim 1, wherein the composition is formulated as a solution, gel, lotion, cream or ointment.

5. The method of claim 1 wherein the composition is topically applied in an amount and for a period of time sufficient to enhance the rate the skin desquamation.

6. The method of claim 5 wherein the topical application is on at least a daily basis.

7. A method of increasing the rate of mammalian skin desquamation comprising the step of topically applying to the skin a composition comprising a first organic acid selected from the group consisting of glycolic, malic, citric and salts thereof and mixtures thereof and acerola cherry fermentate containing a second organic acid wherein the acerola cherry fermentate enhances the rate of skin desquamation achieved by the first organic acid.

8. The method of claim 7 wherein the acerola cherry fermentate causes only slight additional skin irritation when the composition is applied to the skin.

9. The method of claim 7 wherein the acerola cherry fermentate comprises from about 1% to about 5% by weight of the composition based on the whole weight of the composition.

10. The method of claim 7 wherein the acerola cherry fermentate contains no more than 5% by weight of the second organic acid based on the weight of the acerola cherry fermentate.

11. A method of increasing human skin exfoliation rate of mammalian skin achieved by a first organic acid selected from the group consisting of glycolic, malic, citric and salts thereof and mixtures thereof comprising the step of adding acerola cherry fermentate, wherein the acerola cherry fermentate contains a second organic acid in an amount no greater than 5% by weight of the acerola cherry fermentate.

12. The method of claim 11 wherein the acerola cherry fermentate causes only slight additional skin irritation when the composition is applied to the skin.

13. The method of claim 11 wherein the acerola cherry fermentate contains no more than 2% by weight of the second organic acid based on the weight of the acerola cherry fermentate.

* * * * *

UNITED STATES PATENT AND TRADEMARK OFFICE
CERTIFICATE OF CORRECTION

PATENT NO. : 6,074,647
DATED : June 13, 2000
INVENTOR(S) : A. C. Zimmerman et al.

It is certified that error appears in the above-identified patent and that said Letters Patent is hereby corrected as shown below:

<u>Title page, Page 3,</u>
<u>Column 2,</u>
After line 17, insert the following reference:

-- Photocopy of front and back of product container, Vaseline® Brand Intensive Care® Lotion. --.

Signed and Sealed this

Ninth Day of October, 2001

*Attest:*

*Nicholas P. Godici*

*Attesting Officer*

NICHOLAS P. GODICI
*Acting Director of the United States Patent and Trademark Office*